United States Patent
Van der Linden et al.

(10) Patent No.: US 6,330,480 B1
(45) Date of Patent: Dec. 11, 2001

(54) PLASTICALLY DEFORMED MEDICAL ELECTRODE WITH RELEASABLE CONDUCTIVE CABLE

(75) Inventors: Jan Van der Linden, Saltsjöbaden; Lars Bengtsson, Stockholm; Carl Engblom, Nynäshamn; Bengt Welander, Bromma, all of (SE)

(73) Assignee: Cardia Innovation AB, Stockholm (SE)

( * ) Notice: Subject to any disclaimer, the term of this patent is extended or adjusted under 35 U.S.C. 154(b) by 0 days.

(21) Appl. No.: 09/308,542
(22) PCT Filed: Nov. 20, 1997
(86) PCT No.: PCT/SE97/01951
  § 371 Date: Jul. 9, 1999
  § 102(e) Date: Jul. 9, 1999
(87) PCT Pub. No.: WO98/22180
  PCT Pub. Date: May 28, 1998

(30) Foreign Application Priority Data

Nov. 21, 1996 (SE) .................................... 9604268

(51) Int. Cl.$^7$ ........................................ A61N 1/05
(52) U.S. Cl. ................. 607/115; 607/129; 607/130; 607/116; 607/149; 600/374; 600/375; 600/372; 600/386
(58) Field of Search .................. 607/115, 116, 607/119, 129, 130, 149, 152; 600/372, 373, 374, 375, 377, 386, 393, 394

(56) References Cited

U.S. PATENT DOCUMENTS

| | | |
|---|---|---|
| 3,654,933 | 4/1972 | Hagfors ........................... 128/418 |
| 3,999,555 | 12/1976 | Person ............................. 128/418 |
| 4,030,509 | 6/1977 | Heilman et al. ................ 128/419 D |
| 4,144,889 | 3/1979 | Tyers et al. ....................... 128/418 |
| 4,323,081 | 4/1982 | Wiebusch ......................... 128/785 |
| 5,249,574 | 10/1993 | Bush et al. .............................. 607/9 |
| 5,527,358 | 6/1996 | Mehmanaesh et al. ............ 607/129 |
| 5,782,901 | 7/1998 | Praeger ............................... 607/130 |
| 5,849,033 | 12/1998 | Mehmananesh et al. .......... 607/129 |

FOREIGN PATENT DOCUMENTS

| | | |
|---|---|---|
| 1 520 351 | 8/1978 | (GB) . |
| 2 020 981 A | 11/1979 | (GB) . |
| 364 872 | 3/1974 | (SE) . |
| 95/19803 | 7/1995 | (WO) . |
| 96/26675 | 9/1996 | (WO) . |

*Primary Examiner*—Kennedy Schaetzle
(74) *Attorney, Agent, or Firm*—Greer, Burns & Cain, Ltd.

(57) ABSTRACT

An electrode device intended for medical equipment and arranged to be attached to a tissue of a body part of a patient, the electrode device including a clamping member, wherein the clamping member also includes a relatively thin metal sheet to be brought into an electrical connection with the body part, and is also configured and arranged to connect an electric conductive cable member to the clamping member for establishing an electric connection with the medical equipment, the connection being provided in such a way that the cable member is releasably connected to the clamping member, wherein the metal sheet forms a clip, which is arranged to be clamped to the body part by plastic deformation of the metal sheet without extending through the tissue and in such a way that electric signals are transferable between the medical equipment and the body part.

18 Claims, 6 Drawing Sheets

PLASTICALLY DEFORMED MEDICAL ELECTRODE WITH RELEASABLE CONDUCTIVE CABLE

TECHNICAL FIELD OF THE INVENTION AND PRIOR ART

The present invention relates to an electrode device according to the preamble of claim 1.

Such electrode devices may be used in many different applications for medical short and/or long term treatment and diagnosis. Even if the following description first of all is directed to the problem occurring in relation with heart pacing and in particular atrium pacing, it is to be noted that the present invention not in any way is restricted to these applications but may be used in all situations where an electrode is to be attached to a body part of a patient. The invention is applicable to human beings as well as animals. The word pacing means stimulation of a body part by means of electric impulses at a desired frequency.

After a heart surgery, a too low and thus a suboptimal heart frequency is often observed among many patients. Usually, the heart frequency is then increased by breaking a so called beta blockade with a competitive anti-beta blocker or by drugs with a frequency increasing effect. The problem with these drugs is that they at the same time increase the myocardial oxygen consumption (in comparison with pacing only), which leads to an increased myocardial injury when the perfusion of the heart tissue is restricted or compromised, which for example is the case after an infarct. A better alternative is to stimulate directly the function of the heart (pacing) via external pacemaker electrodes attached to the surface of the heart, which causes less influence on the myocardial oxygen consumption than with inotropes/beta-agonists. The pacemaker electrodes are attached to the surface of the atrium and/or the ventricle and are removed by being pulled out through the skin. In the cases, when the conduction between the atrium and the ventricle is intact, which is the case at approximately 80–90% of all patients, electrodes on the surface of the atrium (pacing of atrium) are used in the first place. In this case, the heart's own conduction is used and thereby a synchronising according to the body proper between the atrium and the chamber is obtained.

However, in the case that the conduction between the atrium and the ventricles does not work, so called AV-block III, ventricle pacing has to be used. This occurs above all in connection with the operation of the mitral or aortic valve, since a swelling, bleeding or more permanent injury with respect to the conduction between the ventricles and the atria then may occur. Frequently, these problems with the conduction are temporary and they decrease after a few days when the swelling of the tissue has gone down. In these cases, ventricle pacing is used but furthermore atrium pacing ought to be used and the ventricle pacing ought to be synchronised to the latter in order to obtain an optimal effect. In particular, these measures concern patients with thickened ventricle walls, so called ventricular hypertrophy (due to hypertension or for example aortic stenosis) or patients with a seriously reduced function of the ventricle. These two categories of patients are highly dependent on the contraction of the atrium. A poorly functioning left ventricle is stiff and is not so easily filled as a healthy ventricle. The contraction of the atria leads to an improved filling of a stiff ventricle and this may be decisive in case of a marginal heart function directly after a heart surgical operation. The cardiac output of the heart may be increased with approximately 25% by stimulating the atria synchronisely with the ventricles in comparison with a mere stimulation of the ventricle.

Thus, it may be established that much can be gained by regular atrium pacing of patients after heart surgical operations, irrespective of the existence of a conduction block. However, due to the structure of the tissue of the atria and due to the construction of the electrodes and the method by which they are attached in the atrium, external atrium electrodes are often not used during heart surgery.

The most common a trial pacemaker electrodes consist of simple wires which, via thin sutures, are attached to the surface of the atrium by sewing. It is often difficult from a surgical point of view to sew such electrode wires without the appearance of a bleeding and at the same time to obtain a low electrical threshold value, i.e. a voltage required to provide stimulation of the heart. The technical survival of these electrodes is usually short, often not even twentyfour hours due to a quickly increasing threshold value, i.e. the voltage has to be increased to maintain the stimulating effect. Furthermore, there is a considerable risk for bleedings during this time period and a certain risk for new bleedings when the electrodes are removed.

It is also known to use an electrode with a silver contact from which a helically shaped plastic wire extends. The plastic wire is provided with a needle at its end and is sewed onto the tissue by being extended backwards and forwards through the atrium wall. In such a way the silver contact is kept in place and abuts to the wall closely. After sewing of the plastic wire, the needle is removed. This electrode has a longer time of survival and leads to a lower threshold value in most cases compared to prior technique. A disadvantage with this technique is the risk for dislocation and the fact that the electrode is not easy to attach in such a way that a low threshold value is obtained without any damage of the tissue with a following bleeding.

U.S. Pat. No. 4,144,889 discloses an electrode device intended to be attached to the heart and comprising a releasable cable member and an electrode member for gripping the heart tissue. This document discloses two different embodiments for the attachment of the electrode member. According to the first one, the electrode member is sewed by means of a suture, which extends into the heart tissue and according to the other embodiment, the electrode member is clamped by means of two clamping parts, These clamping parts are mounted to a metal strip forming the electrode proper for transferring a voltage to the heart. The metal strip is embedded between two silicon rubber plates. The first clamping part is attached to the side of the strip facing the heart tissue and bent to a C-shape and is intended to penetrate the heart tissue when the electrode device is applied thereto. The other clamping part is located on the opposite side of the metal strip and has been given a folded shape by means of "spring tempering". The other clamping part projects from the metal strip through holes in the outer silicon rubber plate. By application of the electrode device, the other clamping part is compressed in such a manner that the metal strip is compressed and the first clamping part penetrates the hearts tissue.

To sum up, the lack of suitable attachment devices and attachment methods leads to the matter of fact that the atrium pacing is not used in an optimal way in connection with heart surgery in spite of the medical advantages this treatment could give.

SUMMARY OF THE INVENTION

The object of the present invention is to remedy the above discussed problems and to provide a device affording a simpler way of attachment of an electrode to a body part. Furthermore, it is aimed at a reliable attachment and a reduced risk for injuries and bleedings on the body part in relation to prior known methods.

This object is achieved by the electrode device initially mentioned and which discloses the features specified in the claim 1.

Consequently, the solution of the invention offers a very simple way of attaching an electrode to a body part. By such a clamping member, the electrode may be attached very quickly to the body part by compressing the clamping member by hand or by means of a tool, onto a part of the tissue of the body part. Since it is not necessary for such a clamping member to extend through the tissue of the body member, which for example is the case when the electrode is attached by means of sewing technique, the risk for bleedings in the body part is reduced. This reduced risk for bleedings is of great importance and facilitates the attachment of the electrode device according to the invention to for example an atrium wall of a heart, which is very thin and where bleedings can lead to devastating consequences for the quick recovery of the patient. Consequently by the electrode device according to the invention, the medical treatment by means of pacemakers may in a very significant way be facilitated and this method of treatment may be used in situations and for patients for which it by prior techniques was out of question. Furthermore, by the design according to the invention a simple construction is obtained, in which the metallic piece of material forms both a clip and an electrode and in addition is provided with means for the attachment of the cable member.

According to an embodiment of the invention, said connecting means is provided in such a way that the cable member is releasably connected to the clamping member, when it is desired to measure temporarily for example an electric activity in a body part or treating a patient by electric impulses, as by atrium pacing. The cable member may then, after the treatment being finished, be removed from the clamping member, which according to accepted medical practice is left in the body of the patient. Thereby, said connecting means may advantageously be arranged in such a way that the force required for releasing the cable member from the clamping member is essentially lower than the force required for releasing the clamping member from the body part to which the clamping member is clamped.

According to a further embodiment of the invention, said connecting means comprises at least one passage through which the cable member is extensible. Such a passage may in a simple way be shaped in such a manner that the cable member is attached by a desired force. The passage may be realised in many different ways. Advantageously, said connecting means may comprise a plurality of passages which are provided in such a way in relation to each other that the cable member is extensible through said passage in a non-linear path. In such a way, the holding force is determined by the deformation of the cable which is necessary for its removal from the clamping member and through the different passages. Suitably, said path may thereby be essentially zigzag-shaped. According to a further embodiment, said connection means comprises at least one wire which is extended over a surface, said passage being formed by an interspace between the wire and the surface. Advantageously, said connecting means may thereby comprise a plurality of successively extended wires, every second passage being formed by said interspace and the intermediate passages being formed by the location of the cable member on the side of the respective wire, which faces away from the surface. According to a further embodiment, said connecting means comprises at least one hole forming said passage and provided in said piece of material. This embodiment is from a manufacturing point of view very simple and may be realised by punching a number of holes in a sheet-like part of the clamping member. According to a further embodiment, said connecting means comprises a net-like structure formed by a metallic wire, said passage being formed by an interspace between the wires in this structure. According to a further embodiment, said connecting means comprises a tubular sleeve which forms said passage. Such a sleeve may be manufactured with such a tolerance that the required removing force of the cable member is essentially predetermined. The tubular sleeve may comprise an essentially straight passage or a bent one.

According to a further embodiment of the present invention, said connecting means comprises a portion with a number of hook-like members and the cable member comprises a number of thin wires each gripped by at least one hook-like member.

According to a further embodiment of the present invention, the clamping member comprises two clamping portions being displaceable in a direction towards each other and arranged to engage at least one part of the tissue of said body part therebetween. According to an embodiment, said connecting means may thereby be arranged at one of said clamping portions. According to another embodiment, said connecting means may be formed by the clamping portions being displaceable towards each other. According to a further embodiment, said connecting means may be provided to be clamped between said clamping portions. This embodiment is suitable for a tubular sleeve which forms said passage.

According to a further embodiment of the present invention, at least one on the clamping portions comprises an uneven surface, facing against the other clamping portion. In such a way a proper electric contact is ensured between the electrode device and the body part, which means that the voltage required for providing electric stimulation in connection with for example pacing may be kept on a relatively low level. In such a way it is also possible to sense very feeble electric impulses in the body part. Furthermore, by such an uneven or roughened surface improved gripping of the body part by the clamping member is obtained.

According to a further embodiment of the present invention, the clamping member is arranged to be clamped to said body part by means of plastic deformation of the clamping member. Furthermore, the clamping portions may according to an embodiment, which is advantageous from a manufacturing point of view, be formed by an elongated piece of material, which is foldable around a folding line. Thereby, the clamping portions will be formed by two shanks or legs extending from the folding line.

In an advantageous application of the electrode device according to the present invention, the medical equipment comprises a pacemaker.

BRIEF DESCRIPTION OF THE DRAWINGS

The present invention is now to be described more closely by means of different embodiments, disclosed by way of example, and with reference to the attached drawings.

DESCRIPTION OF PREFERRED EMBODIMENTS OF THE INVENTION

Figure 1:
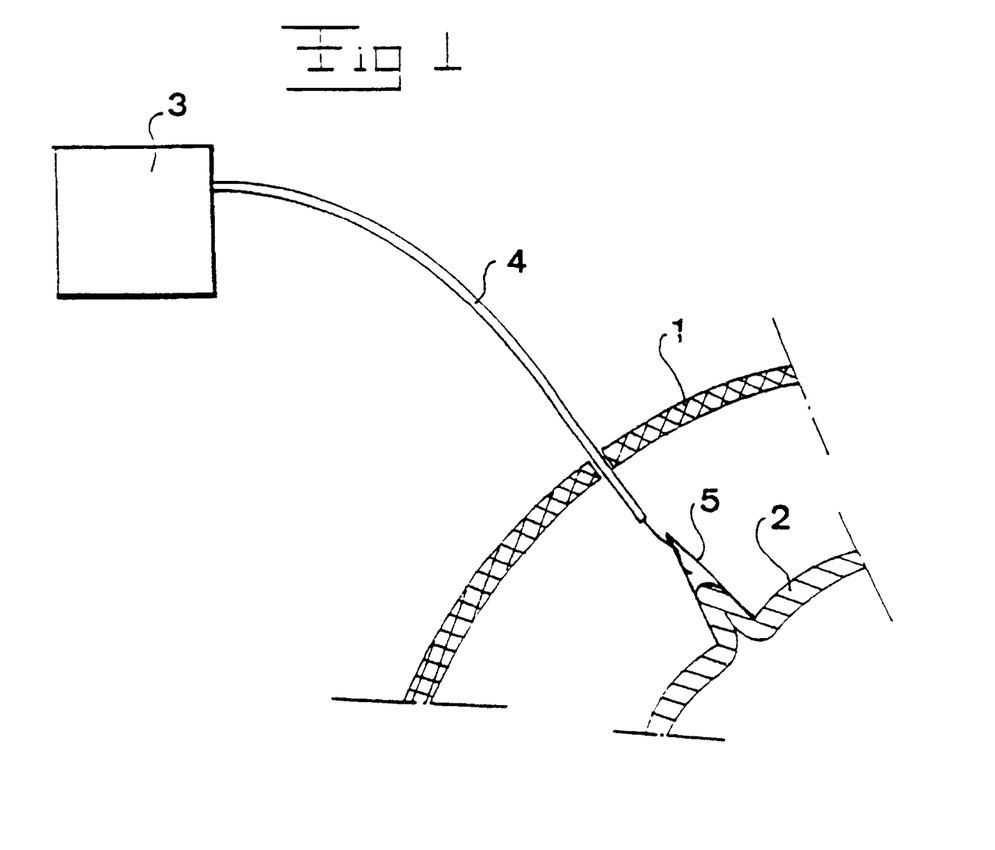
FIG. 1 shows a schematical cross-section through a part of a body part of a patient to which an electrode device according to the present invention is attached.

FIG. 1 shows schematically a cross-section through a body of a patient, 1 representing the skin and 2 an atrium wall of the heart of the patient. 3 denotes a medical equipment which in the example disclosed consists of a pacemaker. The pacemaker 3 is connected to the atrium wall 2 by an electrode device comprising a cable member 4 and a clamping member 5 which is arranged to be clamped to the atrium wall. Consequently, electric impulses may be transferred from the pacemaker 3 to the atrium wall 2 through the cable member 4 and the clamping member 5 for stimulating the action of the heart. As will be described in more detail below, the cable member 4 is releasably attached to the clamping member 5. Consequently, it is possible, after the treatment by the pacemaker 3 is finished, to remove the cable member 4 from the clamping member 5 and out through the skin 1. Thereby, the clamping member 5 remains on the atrium wall 2. It is here to be noted that it is clinically acceptable to leave such clamping members 5 in the body after a treatment has been finished.

It is also to be noted that the electrode device according to the invention may be attached to other body parts than the atrium wall 2 of a heart. For example to other parts of the heart, to kidneys for electrical stimulation of these or to ganglions for alleviation of pain of a patient by electrical stimulation. Also other body parts may be subject for the electrode device according to the invention. Furthermore, it is to be noted that other medical equipment than pacemakers may be subject for connection to any body part by means of the electrode device according to the invention. It may for instance be an electric measuring equipment for measuring electric impulses in any body part of a patient.

Figure 2:
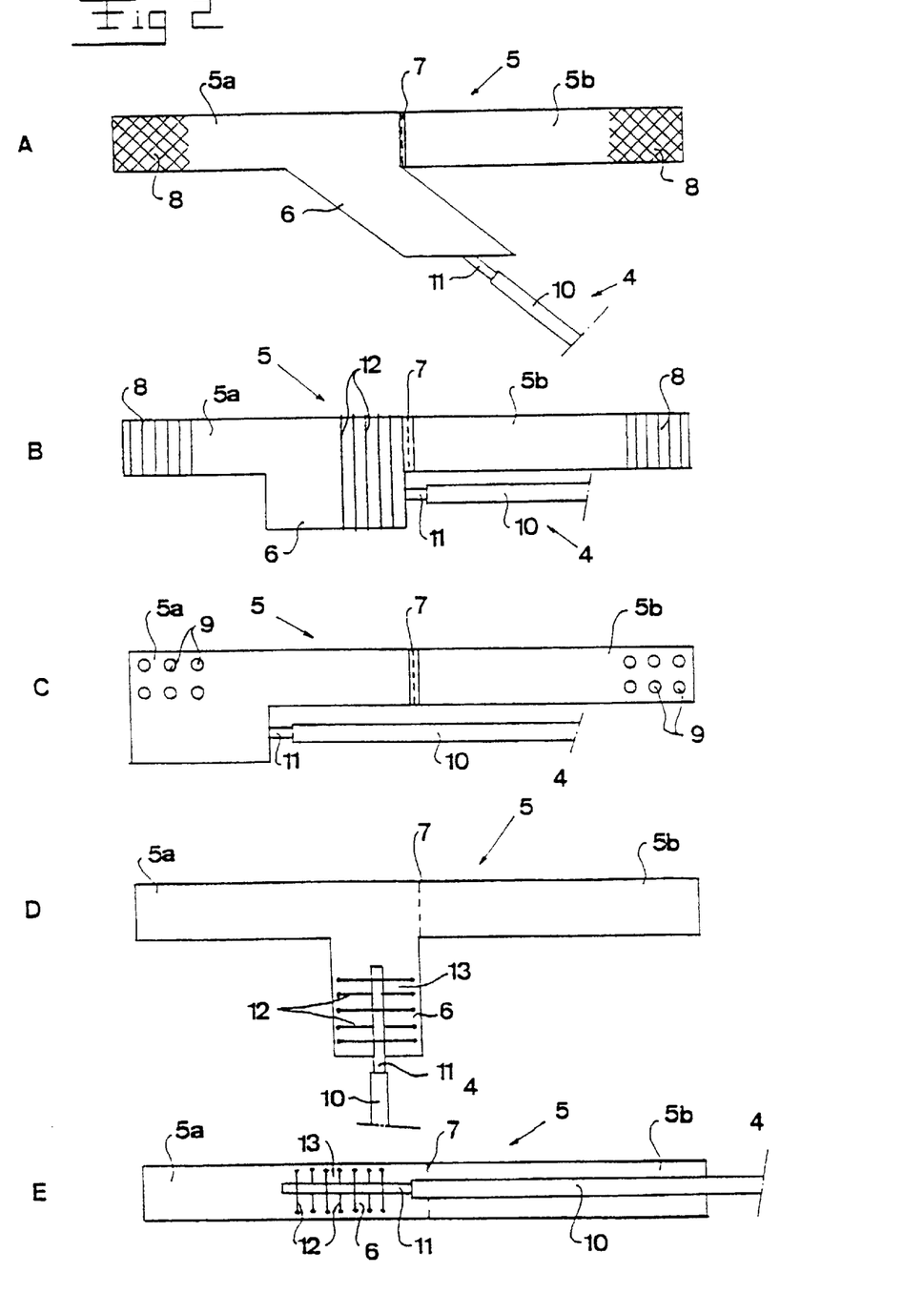
FIGS. 2A–2E show different variants of a clamping member according to a first embodiment of the invention.
Figure 3:
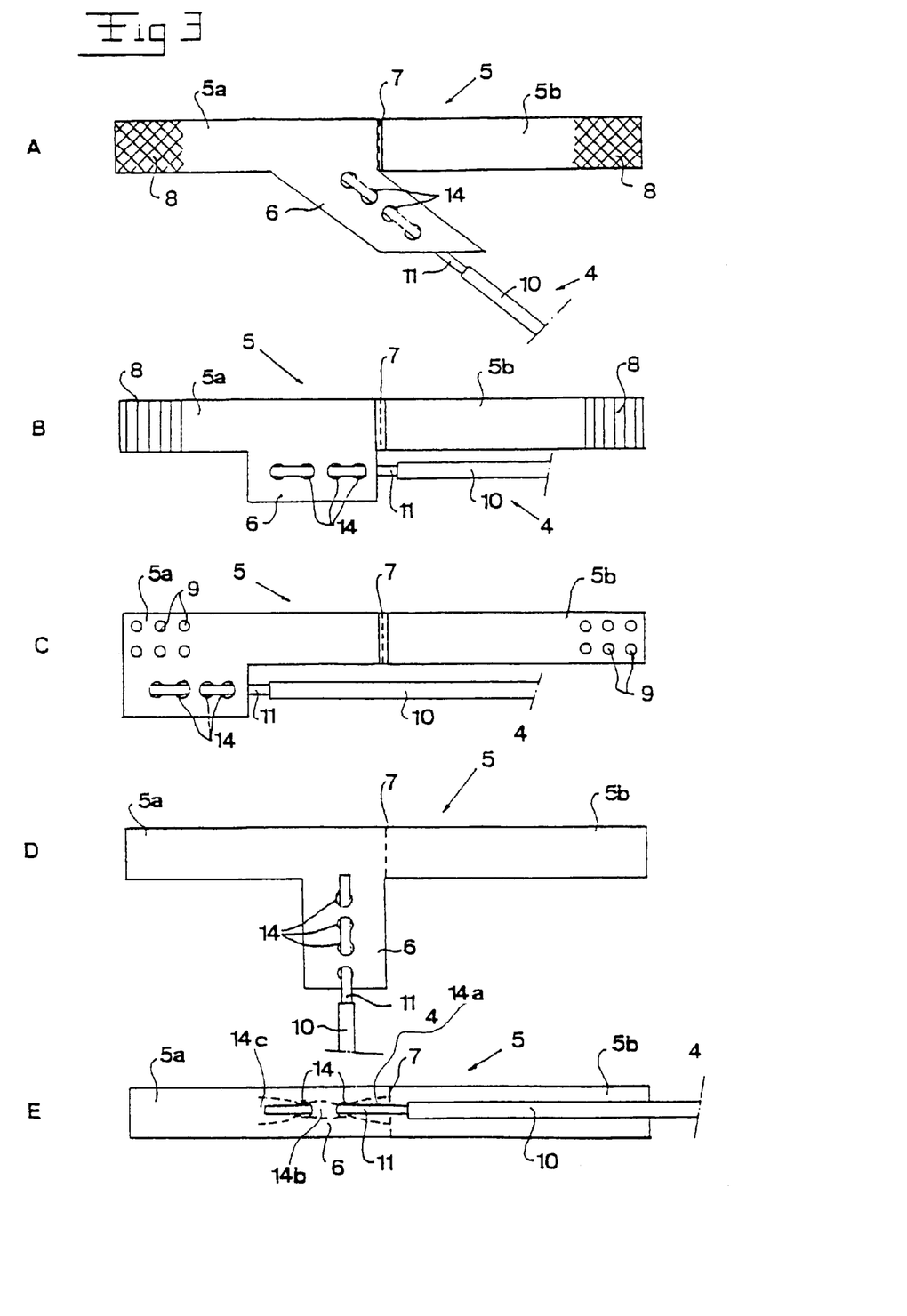
FIGS. 3A–3E show different variants of a clamping member according to a second embodiment of the invention.
Figure 4:
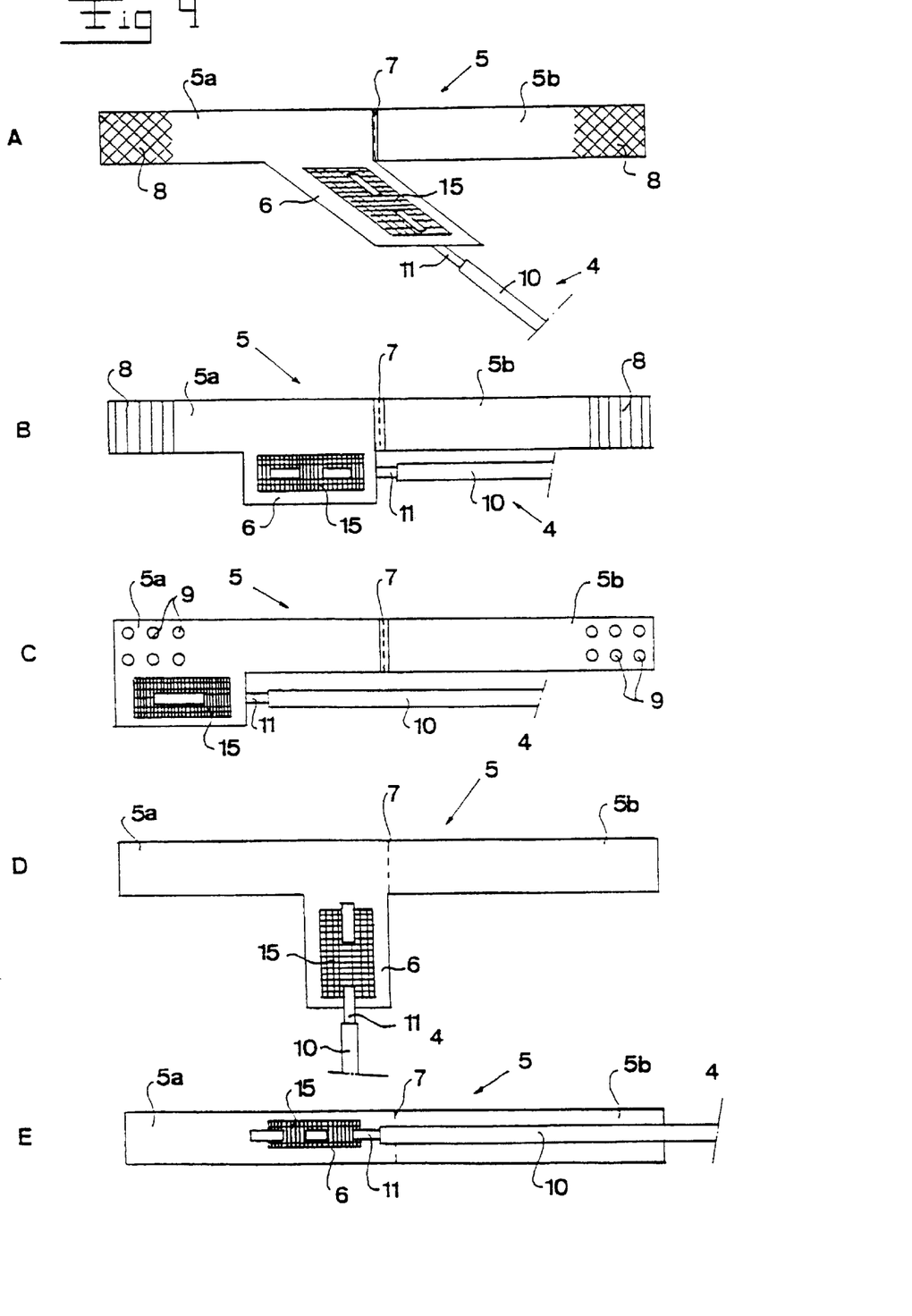
FIGS. 4A–4E show different variants of a clamping member according to the third embodiment of the invention.
Figure 5:
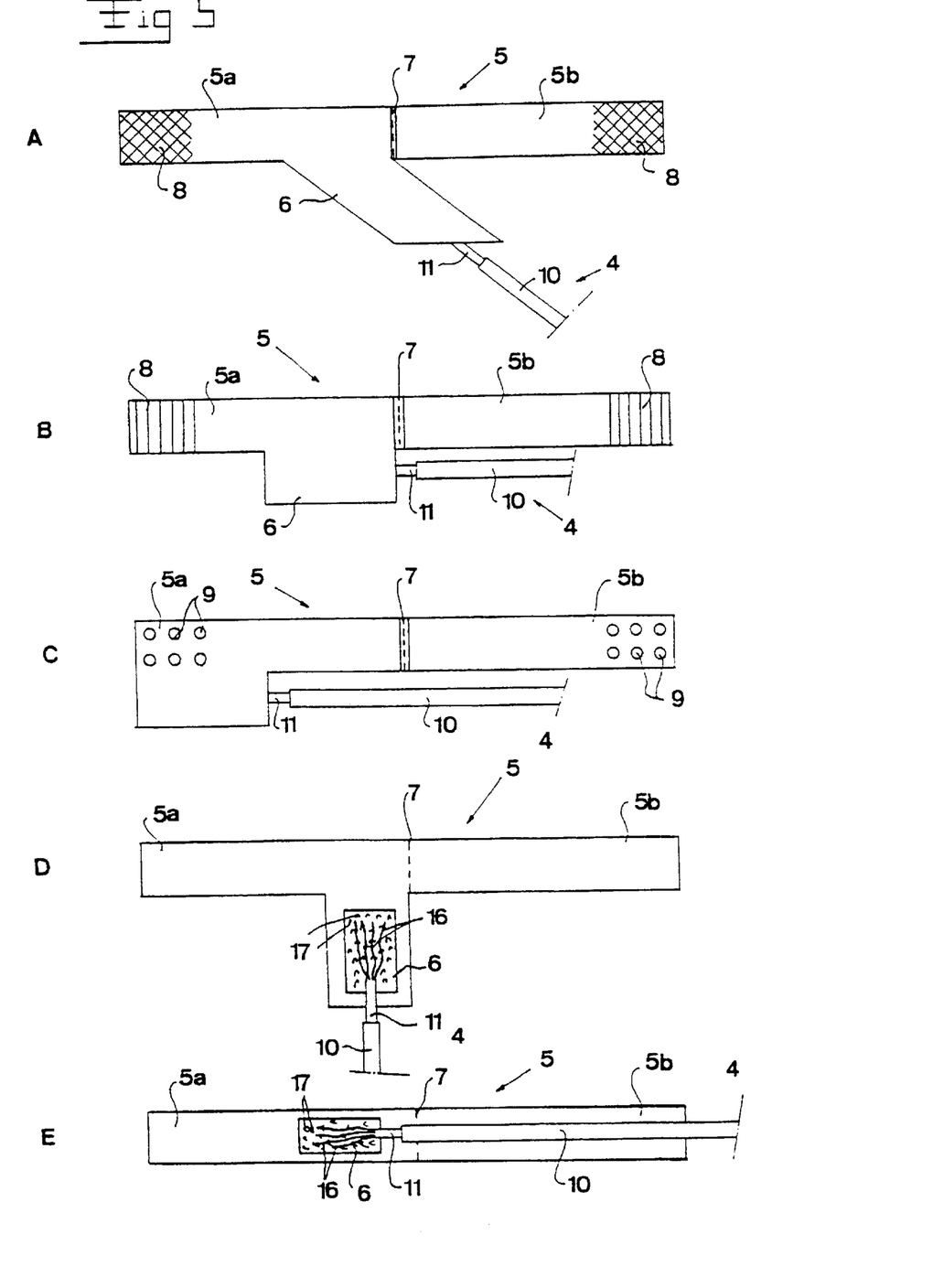
FIGS. 5A–5E show different variants of a clamping member according to a fourth embodiment of the invention.

FIG. 2 shows more in detail the clamping member 5 according to a first embodiment. This first embodiment is shown in FIG. 2 in five different variants A–E, A–C showing the clamping member 5 seen from below and D–E showing the clamping member seen from above. The clamping member 5 comprises means for releasably connecting the cable member 4 to the clamping member 5. These means comprise a connecting portion 6 to which the cable member 4 is releasably attached. The clamping member 5 is in the example shown produced in one piece and in an electric conductive material, preferably a metal or alloy of metals, for instance silver, titanium, stainless steel, gold, platina etc. Furthermore, the clamping member 5 has, in the example shown, an elongated shape and a relatively thin thickness, i.e. the clamping member 5 is formed by an elongated, relatively thin metal sheet, which is foldable around a folding line 7 being surrounded by a weakened or a thinner portion of the material extending over the width of the clamping member 5 along the folding line 7. Consequently, the clamping member 5 can be folded along the folding line 7 in such a manner that two clamping portions or legs 5a, 5b are formed. This folding or compressing of the clamping member 5 is preferably provided by means of a plier-like tool (not shown) and result in a plastic deformation of the clamping member 5 in the area of the folding line 7. By this plastic deformation the clamping member 5, such as the metal sheet proper, retains in its compressed state after the tool has been removed. With the purpose to provide a proper grip between the clamping member 5 and that body part 2, to which the clamping member 5 is to be attached, each clamping portion 5a, 5b has a portion 8 with an uneven surface. This uneven surface 8 may be provided in many different ways, for instance by roughening the surface, milled grooves extending either across the length of the clamping member, as is shown in FIG. 2B, or diagonally across the elongated extension of the clamping members 5 in one or two directions, as is shown in FIG. 2A. In FIG. 2C the uneven surface is formed by small projecting portions 9, which for instance may be provided by pressing. Furthermore, a purpose of the uneven surface 8 is to provide a good electric contact between the clamping member 5 and the body part 2, to which the clamping member 5 is to be attached, in order to maintain a low electrical threshold voltage.

The cable member 4 comprises an isolation 10 and an electric wire 11 provided inside the isolation. At the end of the cable member 4, the isolation 10 is removed and the electric wire 11 is attached to the connection portion 6.

According to the first embodiment the connecting portion 6 comprises a number of wires 12 extended over a surface 13 of the connecting portion 6. The wires 12 are preferably produced in any electric conductive material as a metal or alloy of metals, for instance silver, titanium, stainless steel, gold, platina etc. The wires 12 may be soldered in their both ends to the surface 13 as is shown in FIG. 2D and 2E. However, the wires 12 may also be wound around the connecting portion 6 in a helical path or in closed loops, see FIG. 2B. The cable member 4 is attached to the clamping member 5 by the introduction of the electric wire 11 between the wires 12 and the surface 13. As appears from FIG. 2D and 2E the electric wire 11 is thereby introduced under every second wire 12 and is lying above the intermediate wires 12. In such a way the electric wire 11 will extend in a zigzag-shaped path. It is to be noted that the electric wire 11 of course also may extend irregularly over or under the wires 12, for instance under two, over one, under two etc. This being valid particularly in the cases that the number of wires 12 is higher than the number disclosed. By the clamping arrangement shown, a good electric contact between the electric wire 11 and the clamping member 5 is ensured and at the same time it is possible to release the cable member 4 out of the grip of the connecting portion 6 of the clamping member 5 by means of a moderate predetermined force The different embodiments 2A–2E show different locations of the connecting portion 6 and by the choice of such a location one may decide in which direction the cable member 4 is to be released. Depending on the application of the electrode device according to the invention, such a suitable location may be chosen.

FIGS. 3A–3E show a second embodiment of the invention which differs from the first one by the design of the connecting portion 6. According to the second embodiment, the connecting portion 6 comprises a number of successively located holes 14 which may be punched out of the clamping member 5. The cable member 4 is releasably attached to the connecting portion 6 by the electric wire 11 being introduced into or threaded through the holes 14 in a zigzag-shaped extension. This embodiment is from a manufacturing point of view very advantageous and a very good electric contact is obtained at the same time as the removability of the cable member 4 by a predetermined force may be ensured. The embodiment of FIG. 3E includes merely two holes 14. In order to facilitate removal of the electric wire 11, the sheet material of the clamping portion Sa of the clamping member 5 has been deformed in the areas adjacent to the holes 14. From above, as disclosed in FIG. 3E, there is a first depression 14a between the folding line 7 and the first hole 14. Furthermore, there is a second depression 14b from below between the two holes 14. There may also be a third depression 14c from above between the second hole 14 and the outer edge of the clamping portion 5a. By means of these alternating depressions 14a, 14b, the path of the electric wire 11 through the holes is straightened in comparison with the embodiment of FIG. 3A–D.

FIGS. 4A–4E show a third embodiment which also differs from the previous embodiments by the design of the connecting piece 6. According to the third embodiment, the connecting piece 6 comprises a net-like structure 15 consisting of a great number of relatively thin wires woven together, which preferably are produced in an electrically conductive material, such as any metal or metal alloy like for instance silver, titanium, stainless steel, gold, platina etc. According to this embodiment, the electric wire 11 of the cable member 4 is simply sewed onto or threaded through the net-like structure 15. Also by this embodiment, a good electric contact between the cable member 4 and the clamping member 5 is obtained at the same time as the removability of the cable member 4 may be guaranteed by simply being pulled out by a force of an essentially predetermined value.

FIGS. 5A–5E show a fourth embodiment in which the connecting piece 6 is provided with a great number of small hook-like members 16. The electric wire 11 comprises a number of wires 17 which are twinned together. These wires 17 are clamped in the connecting portion 6 in such a way that each of the wires 17 is engaged by one or more of the hook-like members 16. Consequently, the hook-like members 16 form passages for the wires 17 of the electric wire 11 and at the release of the cable member 4, the wires 17 may be pulled out of these passages. The hook-like members 16 are produced of an electric conductive material, preferably a metal or alloy of metals such as silver, titanium, stainless steel, gold, platina etc.

Figure 6:
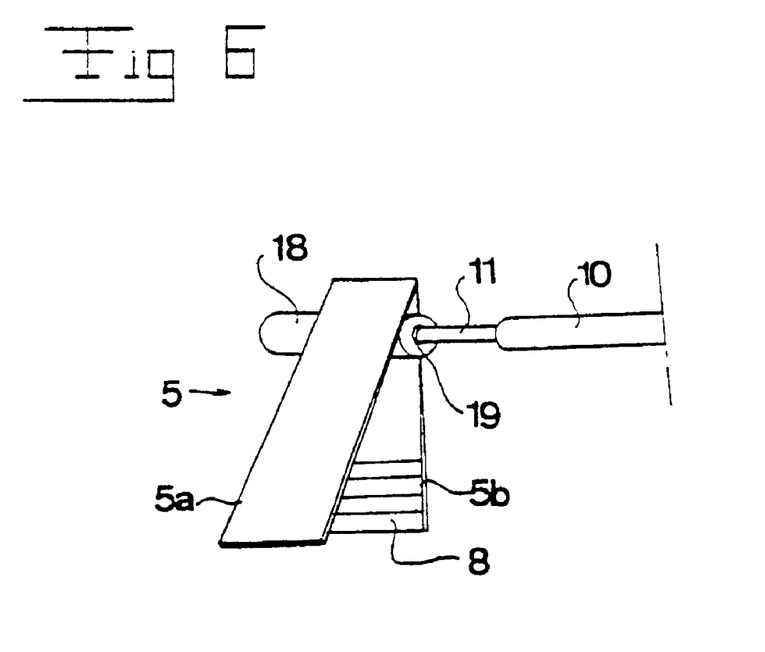
FIG. 6 shows a clamping member according to a fifth embodiment of the invention.

FIG. 6 shows a fifth embodiment of the invention in which the connecting portion 6 comprises a tubular sleeve 18 which is attached to the clamping member 5. The tubular sleeve 18 is produced in an electric conductive material, preferably a metal or alloy of metals such as silver, titanium, stainless steel, gold, platina etc. The tubular sleeve 18 comprises a passage or a hole 19 through which the electric wire 11 of the cable member 4 extends. The hole 19 is dimensioned in such a manner that the electric wire 11 has a good electric contact with the tubular sleeve 18 and is removable by a predetermined force. The tubular sleeve 18 may be attached to the clamping member 5 by for instance soldering to either the upper side or the underside. Furthermore, the tubular sleeve 18 may be arranged to be clamped between the clamping portions 5a, 5b of the clamping member 5 in connection with the clamping thereof to the body part 2. In this latter case, it is essential that the tubular sleeve 18 does not permit any deformation thereof due to the force applied thereon during the compressing of the clamping member 5.

In the embodiments which are shown in FIGS. 2–6, it is possible to preproduce the electrode device, i.e. the cable member 4 is delivered clamped to the clamping member 5 according to the above shown manner.

Figure 7:
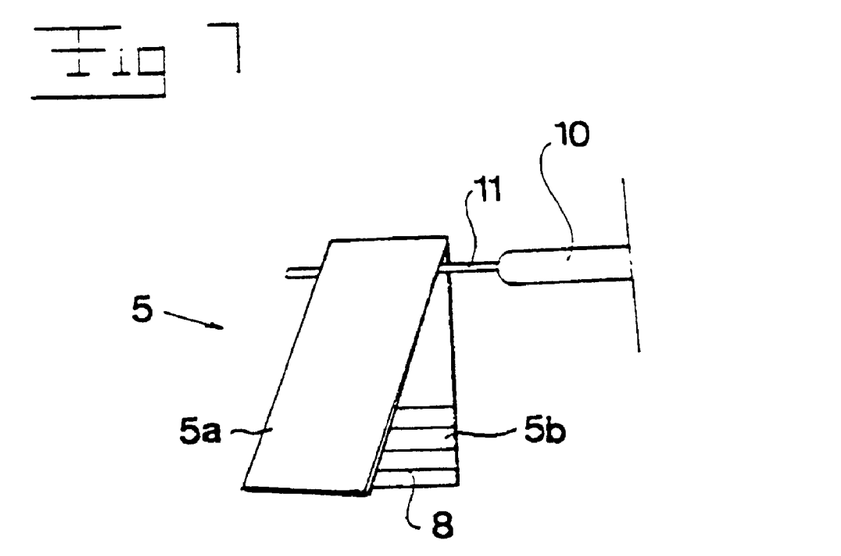
FIG. 7 shows a clamping member according to a sixth embodiment of the invention.

FIG. 7 shows the sixth embodiment of the invention, in which the connecting portion 6 is formed by the two clamping portions 5a, 5b of the clamping member 5 in such a way, that the electric wire 11 of the cable member 4 simply is clamped or engaged between these portions 5A, 5B as they are compressed together. This fixing of the electric wire 11 to the clamping member 5 may be performed as a preparatory measure prior to the attachment to the body part, or in connection with said attachment to the body part.

The present invention is not restricted to the different embodiments shown above but may be varied and modified within the scope of the following claims. For instance, it is to be noted that the clamping member 5 shown not only may be used for a temporary attachment of an electrode to a body part but also is suitable for a more permanent attachment of electrodes. It is of course unambiguous for a person skilled in the art that the force required for releasing the cable member may be varied and for instance be increased by an increase of the number of holes 14 according to the second embodiment. In such a way, the electrode device according to the invention may be adapted to a more permanent use.

It is to be noted that the clamping member 5 may have a relatively moderate dimension, in the order of 10–30 mm, and therefore it is not only attachable to external body parts or in connection with open surgery but also suitable for use in connection with minimal invasive surgery, keyhole surgery, thoracoscopic surgery and/or pericardioscopic surgery. In particular, it is to be noted that these surgery methods are suitable in connection with a permanent attachment of the electrode device according to the invention.

What is claimed is:

1. An electrode device intended for medical equipment and arranged to be attached to a tissue of a body part of a patient, the electrode device comprising a clamping member, which comprises a relatively thin metal sheet to be brought into an electrical connection with said body part, and means arranged to connect an electric conductive cable member to said clamping member for establishing an electric connection with the medical equipment, said connecting means being provided in such a way that the cable member is releasably connected to the clamping member, wherein said metal sheet forms a clip, which is arranged to be clamped to said body part by means of plastic deformation of said metal sheet without extending through the tissue and in such a way that electric signals are transferable between the medical equipment and said body part.

2. An electrode device according to claim 1, wherein said connecting means are arranged in such a manner that the force required for releasing the cable member from the clamping member is substantially lower than the force required for releasing the clamping member from the body part to which the clamping member is clamped.

3. An electrode device according to claim 1, wherein said connecting means comprises at least one passage through which the cable member is extensible.

4. An electrode device according claim 3, wherein said connecting means comprises a plurality of passages which are provided in such a way in relation to each other that the cable member is extensible through said passages in a non-linear path.

5. An electrode device according to claim 4, wherein said path is essentially zigzag-shaped.

6. An electrode device according to claim 3, wherein said connection means comprises at least one wire which is extended over a surface and said passage is formed by an interspace between the wire and the surface.

7. An electrode device according to claim 6, wherein said connecting means (6) comprises a plurality of successively extended wires, every second passage being formed by said interspace and the intermediate passages being formed by the location of the cable member on the side of the respective wire, which faces away from the surface.

8. An electrode device according to claim 3, wherein said connecting means comprises at least one hole forming said passage and provided in said piece of material.

9. An electrode device according to claim 3, wherein said connecting means comprises a net-like structure formed by a metallic wire and said passage is formed by an interspace between wires in this structure.

10. An electrode device according to claim 3, wherein said connecting means comprises a tubular sleeve which forms said passage.

11. An electrode device according to claim 1, wherein said connecting means comprises a portion with a number of hook-like members and the cable member comprises a number of thin wires each gripped by at least one hook-like member.

12. An electrode device according to claim 1, wherein the clamping member comprises two clamping portions being displaceable in a direction towards each other and arranged to engage at least one part of the tissue of said body part therebetween.

13. An electrode device according claim 12, wherein said connection means is arranged at one of said clamping portions.

14. An electrode device according to claim 3, wherein said connecting means are clamping portions configured to be displaceable towards each other.

15. An electrode device according to claim 12, wherein said connecting means is provided to be clamped between said clamping portions.

16. An electrode device according to claim 12, wherein at least one of the clamping portions comprises an uneven surface, facing against the other clamping portion.

17. An electrode device according to claim 12, wherein said clamping portions are formed by an elongated piece of material, which is foldable around a folding line.

18. An electrode device according to claim 1 wherein the medical equipment comprises a pacemaker.

* * * * *